United States Patent [19]

Boller et al.

[11] Patent Number: 4,704,005
[45] Date of Patent: Nov. 3, 1987

[54] DICYANO COMPOUNDS

[75] Inventors: Arthur Boller, Binningen; Martin Petrzilka, Kaiseraugst; Martin Schadt, Seltisberg, all of Switzerland

[73] Assignee: Hoffmann-La Roche Inc., Nutley, N.J.

[21] Appl. No.: 542,297

[22] Filed: Oct. 14, 1983

[30] Foreign Application Priority Data

Oct. 21, 1982 [CH] Switzerland .............. 6124/82
Jul. 28, 1983 [CH] Switzerland .............. 4144/83

[51] Int. Cl.$^4$ .............. G02F 1/13; C09K 19/30; C07C 121/64
[52] U.S. Cl. .............. 350/346; 252/299.5; 252/299.63; 252/299.66; 252/299.6; 350/350 R; 558/419; 558/421
[58] Field of Search .............. 252/299.66, 299.63, 252/299.5; 350/350 R, 250 S, 246; 260/465 F, 465 H; 555/419, 421

[56] References Cited

U.S. PATENT DOCUMENTS

| | | | |
|---|---|---|---|
| 4,279,770 | 7/1981 | Inukai et al. | 252/299.63 |
| 4,368,135 | 1/1983 | Osman | 252/299.63 |
| 4,393,258 | 7/1983 | Sato et al. | 252/299.63 |
| 4,400,293 | 8/1983 | Romer et al. | 252/299.63 |
| 4,415,470 | 11/1983 | Eidenschink et al. | 252/299.63 |
| 4,439,015 | 3/1984 | Rich et al. | 252/299.63 |
| 4,460,770 | 7/1984 | Petrzilka et al. | 252/299.64 |
| 4,479,885 | 10/1984 | Mukoh et al. | 252/299.62 |
| 4,514,317 | 4/1985 | Tuong et al. | 252/299.64 |
| 4,556,745 | 12/1985 | Carr et al. | 252/299.63 |

FOREIGN PATENT DOCUMENTS

| | | | |
|---|---|---|---|
| 19665 | 12/1980 | European Pat. Off. | 252/299.63 |
| 23728 | 2/1981 | European Pat. Off. | 252/299.63 |
| 84194 | 7/1983 | European Pat. Off. | 252/299.63 |
| 85995 | 8/1983 | European Pat. Off. | 252/299.62 |
| 87963 | 9/1983 | European Pat. Off. | 252/299.63 |
| 2937700 | 4/1980 | Fed. Rep. of Germany | 252/299.63 |
| 2939782 | 4/1981 | Fed. Rep. of Germany | 252/299.64 |
| 3237367 | 4/1984 | Fed. Rep. of Germany | 252/299.63 |
| 3317597 | 11/1984 | Fed. Rep. of Germany | 252/299.63 |
| 3410734 | 10/1985 | Fed. Rep. of Germany | 252/299.63 |
| 57-5782 | 1/1982 | Japan | 252/299.63 |
| 57-5780 | 1/1982 | Japan | 252/299.63 |
| 82/00654 | 3/1982 | PCT Int'l Appl. | 252/299.64 |
| 2039937 | 8/1980 | United Kingdom | 252/299.66 |
| 2078727 | 1/1982 | United Kingdom | 252/299.63 |
| 2134110 | 8/1984 | United Kingdom | 252/299.63 |

OTHER PUBLICATIONS

Osman et al., "Stable Liquid Crystals with Large Negative Dielectric Anisotropy-III", Mol Cryst. Liq. Cryst., 82 (Letters), 339-344 (Feb. 1983).

*Primary Examiner*—Teddy S. Gron
*Attorney, Agent, or Firm*—Jon S. Saxe; Bernard S. Leon; George W. Johnston

[57] ABSTRACT

Compounds of the formula:

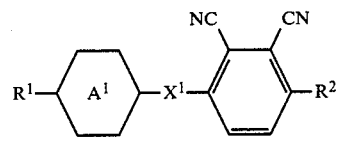

I wherein $R^1$ and $R^2$ are independently straight-chain $C_1$-$C_{12}$-alkyl or when positioned on an aromatic ring $R^1$ and $R^2$ may also independently be straight-chain $C_1$-$C_{12}$-alkoxy, or one of $R^1$ and $R^2$ may also be a group of the formula:

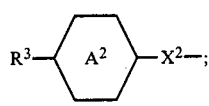

II $X^1$ and $X^2$ are independently single covalent bonds or one of $X^1$ and $X^2$ may also be —CH$_2$CH$_2$—; rings $A^1$ and $A^2$ are independently 1,4-phenylene or, when $X^1$ or $X^2$ is —CH$_2$CH$_2$—, rings $A^1$ and $A^2$ may also independently be trans-1,4-cyclohexylene; and $R^3$ is straight-chain $C_1$-$C_{12}$-alkyl or when positioned on an aromatic ring $R^3$ may also be straight-chain $C_1$-$C_{12}$-alkoxy. Their manufacture and use in liquid crystalline mixtures are described.

9 Claims, No Drawings

DICYANO COMPOUNDS

BACKGROUND OF THE INVENTION

1. Field of the Invention

This invention relates to liquid crystalline compounds and mixtures.

2. Background Description

Liquid crystals have gained considerable importance as dielectrics in indicating devices, since the optical properties of such substances can be influenced by an applied voltage. Electro-optical indicating devices which utilize liquid crystal cells are well known to the person skilled in the art.

Liquid crystals must satisfy a number of requirements in order to be suitable as dielectrics for electro-optical indicating devices. For example, the liquid crystals must have a high chemical stability towards environmental factors (e.g. heat, air, moisture and the like), must be photochemically stable and colourless, must have short response times, must not be too high a viscosity, must have a nematic or cholesteric-type mesophase in all temperature ranges in which the liquid crystal cell is to be operated, and must give a good contrast. Other properties such as, for example, the threshold potential, the dielectric anisotropy and the electrical conductivity must fulfill different conditions depending on the type of cell which is used.

Nematic and cholesteric liquid crystals with negative anisotropy of the dielectric constants ($\Delta\epsilon = \epsilon_\| - \epsilon_\perp < 0$, $\epsilon_\|$ signifying the dielectric constant along the longitudinal molecular axis and $\epsilon_\perp$ signifying the dielectric constant perpendicular thereto) can be orientated in an electric field with their longitudinal molecular axes perpendicular to the field direction. The effect of this orientation is known and is used to control optical transmissivity in various liquid crystal indicators, for example in liquid crystal cells of the light scattering type (dynamic scattering), of the so-called DAP type (deformation of aligned phases) or of the guest/host type (guest host interaction).

The "guest/host cell" comprises essentially a condenser, at least one electrode being transparent and the dielectric being formed from a nematic or cholesteric liquid crystal which contains one or more dichroic colouring substances. Since the colouring substances used mainly have positive dichroism, i.e. the transition moment of the absorption of visible light lies approximately in the direction of the longitudinal molecular axis, the orientation of the liquid crystal with the molecular axes parallel to the surface of the plates generally corresponds to the coloured state and the homeotropic orientation (longitudinal molecular axes perpendicular to the surface of the plates) generally corresponds to the colourless state of the cell. When a liquid crystal with positive dielectric anisotropy is used, its homogeneous orientation (which is achieved by treating the surface of the plates) is arranged homeotropic by the application of a voltage, i.e. the cell is swiched from "coloured" to "colourless." In this manner colourless symbols are shown on a coloured background. On the other hand, when a liquid crystal with negative dielectric anisotropy is used, its homeotropic orientation (by treating the surface of the plates) is arranged parallel to the electrode surfaces by the application of a voltage, whereby the reading of coloured image elements on a colourless background is made possible.

The customary, static operation of liquid crystal indicating devices has in the past been replaced to an increasing extent by the so-called multiplex control. In this case there is mainly used an amplitude-selective multiplex procedure, whereby, however, by the procedures usually used, in general only multiplex ratios of about 1.8 to 1.10 have been attained. However, for the improvement of the multiplex ratio in the multiplex control of liquid indicators, especially of rotation cells and guest/host cells, a two-frequency matrix addressing procedure has been proposed (e.g. German Offenlegungsschriften Nos. 2 856 134 (Great Britain Pat. No. 2 013 014) and 2 907 940 (Great Britain Pat. No. 2 020 075). This makes use of the fact that the dielectric anisotropy of liquid crystals, which upon application of a low frequency voltage have a positive anisotropy of the dielectric constants, is negative in the case of high frequencies. In order to maintain the capacitative loss low, the "cross-over frequency" $f_c$ (dielectric relaxation frequency at which $\epsilon_\| = \epsilon_\perp$) of such liquid crystals should be as low as possible and should not lie above about 20 kHz. Further, the absolute value of the dielectric anisotropie should be as large as possible not only below but also above the cross-over frequency. It has, however, been found that the substances, which are especially suitable for the two-frequency procedure, at frequencies above the cross-over frequency generally have a smaller absolute dielectric anisotropy than below the cross-over frequency. This disadvantage can be eliminated by adding compounds with negative dielectric anisotropy and suitable relaxation behaviour.

A series of liquid crystalline compounds with weakly negative dielectric anisotropy has already been synthesized. On the other hand, still relatively few liquid crystal components with large negative anisotropy of the dielectric constants are known. Moreover, the latter generally have disadvantages, such as, for example, poor solubility in mixtures, high viscosity, high melting points, strong smectic tendencies and chemical instability. There accordingly exists a need for more compounds with negative dielectric anisotropy which further improve the properties of liquid crystal mixtures so that they may be used for an even wider variety of electro-optical purposes.

SUMMARY OF THE INVENTION

The present invention concerns novel dicyanobenzenes of the formula:

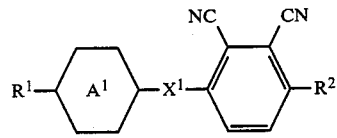

I wherein $R^1$ and $R^2$ signify straight-chain $C_1$-$C_{12}$-alkyl or on an aromatic ring also straight-chain $C_1$-$C_{12}$-alkoxy, or one of $R^1$ and $R^2$ also signifies a group of the formula:

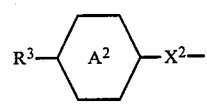

II $X^1$ and $X^2$ denote single covalent bonds or one of $X^1$ and $X^2$ also denotes an ethylene group —$CH_2CH_2$—; rings $A^1$ and $A^2$ represent 1,4-phenylene or, insofar as $X^1$ or $X^2$ denotes an ethylene group —$CH_2CH_2$—, also trans-1,4-cyclohexylene; and $R^3$ signifies straight-chain $C_1$–$C_{12}$-alkyl or on an aromatic ring $A^2$ also straight-chain $C_1$–$C_{12}$-alkoxy.

The invention is also concerned with the manufacture of the compounds of formula I above, their use for electro-optical purposes and liquid crystalline mixtures which contain compounds of formula I.

It has now been found that the compounds of the invention have a large negative anisotropy of the dielectric constants, a good solubility in known liquid crystal mixtures and a relatively low viscosity. They are colourless and have a very good chemical and photochemical stability. Further, with the compounds provided by the invention there can be manufactured mixtures which have an improved melting behaviour and no smectic tendencies or only slight smectic tendencies. They are accordingly especially suitable for improving the properties of liquid crystal mixtures with negative anisotropy of the dielectric constants or of liquid crystal mixtures which are suitable for the two-frequency matrix addressing. They can, however, also be used in mixtures with positive dielectric anisotropy, for example in order to adapt the threshold potential of the electro-optical cell which is used.

DETAILED DESCRIPTION OF THE INVENTION

The invention concerns dicyanobenzenes of the formula:

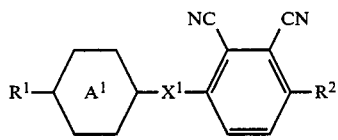

I wherein $R^1$ and $R^2$ are independently straight-chain $C_1$–$C_{12}$-alkyl or when positioned on an aromatic ring $R^1$ and $R^2$ may also independently be straight-chain $C_1$–$C_{12}$-alkoxy, or one of $R^1$ and $R^2$ may also be a group of the formula:

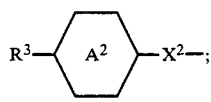

II $X^1$ and $X^2$ are independently single covalent bonds or one of $X^1$ and $X^2$ may also be —$CH_2CH_2$—; rings $A^1$ and $A^2$ are independently 1,4-phenylene or, when $X^1$ or $X^2$ is —$CH_2CH_2$—, rings $A^1$ and $A^2$ may also independently be trans-1,4-cyclohexylene; and $R^3$ is straight-chain $C_1$–$C_{12}$-alkyl or when positioned on an aromatic ring $R^3$ may also be straight-chain $C_1$–$C_{12}$-alkoxy.

These inventive compounds have a large negative anisotropy of the dielectric constants, a good solubility in known liquid crystal mixtures and a relatively low viscosity. They are colourless and have a very good chemical and photochemical stability. Further, mixtures can be manufactured with the inventive compounds which have an improved melting behaviour and no smectic tendencies or only slight smectic tendencies. These compounds are especially suitable for improving the properties of liquid crystal mixtures with negative anisotropy of the dielectric constants or of liquid crystal mixtures which are suitable for the two-frequency matrix addressing. These compounds can, however, also be used in mixtures with positive dielectric anisotropy, for example in order to change the threshold potential of the electro-optical cell which is used.

As used herein, the term "straight-chain $C_1$–$C_{12}$-alkyl" embraces methyl, ethyl, propyl, butyl, pentyl, hexyl, heptyl, octyl, nonyl, decyl, undecyl and dodecyl and the term "straight-chain $C_1$–$C_{12}$-alkoxy" embraces methoxy, ethoxy, propyloxy, butyloxy, pentyloxy, hexyloxy, heptyloxy, octyloxy, nonyloxy, decyloxy, undecyloxy and dodecyloxy.

Unless otherwise indicated, the terms "dielectric anisotropy" or "anisotropy of the dielectric constants" signify in the scope of the present invention the low-frequency ("static") dielectric anisotropy.

The term "aromatic ring" when used in reference to the inventive compounds of formula I, means 1,4 phenylene and/or 2,3 dicyano 1,4 phenylene.

"Halogen" as used herein means flourine, bromine or chlorine.

The term "alkali metal" denotes sodium, potassium and lithium.

Compounds of formula I in which $R^1$ and $R^2$ signify straight-chain $C_1$–$C_{12}$-alkyl or when positioned on an aromatic ring may also signify straight-chain $C_1$–$C_{12}$-alkoxy are preferred. In the case of these bicyclic compounds either $X^1$ denotes a single covalent bond and ring $A^1$ denotes 1,4-phenylene, or $X^1$ denotes an ethylene group and ring $A^1$ denotes 1,4-phenylene, or, preferably, $X^1$ denotes an ethylene group and ring $A^1$ denotes trans-1,4-cyclohexylene.

Preferred compounds are those of formula I in which at least one of $R^1$, $R^2$ or $R^3$ and, more preferably two, signifies $C_1$–$C_{12}$-alkyl. Also preferred are compounds of formula I wherein $R^1$ and $R^2$ signify $C_1$–$C_{12}$ straight-chain alkyl or one of $R^1$ and $R^2$ signify a group of formula II wherein $R^3$ signifies a $C_1$–$C_{12}$ straight-chain alkyl. Especially preferred are those compounds of formula I in which $R^1$ and $R^2$ signify straight-chain alkyl, particularly those in which additionally $X^1$ denotes an ethylene group and ring $A^1$ denotes trans-1,4-cyclohexylene.

Further, preferred compounds are those of formula I in which the alkyl groups contain 3 to 7 carbon atoms, and the alkoxy groups contain 2 to 6 carbon atoms.

More specifically, two especially preferred compounds are 2,3 dicyano-1-[2-(trans-4-pentylcyclohexyl)ethyl]-4-propyl-benzene and 2,3 dicyano-1-[2-(trans-4-pentylcyclohexyl)ethyl]-4-butylbenzene.

Examples of preferred compounds provided by the invention are the compounds of formula I in which $R^1$, ring $A^1$, $X^1$ and $R^2$ have the significances given in Table 1 (C6H4 denotes 1,4-phenylene, C6H10 denotes trans-1,4-cyclohexylene and a single dash (-) for $X^1$ denotes a single covalent bond), as well as the compounds of formula I named in the Examples hereinafter.

TABLE 1

| $R^1$- | $A^1$ | $X^1$ | $R^2$ |
|---|---|---|---|
| C3H7 | C6H4 | — | C3H7 |
| C3H7 | C6H4 | — | C5H11 |
| C3H7 | C6H4 | — | C7H15 |
| C5H11 | C6H4 | — | C3H7 |
| C5H11 | C6H4 | — | C5H11 |
| C5H11 | C6H4 | — | C7H15 |
| C7H15 | C6H4 | — | C3H7 |
| C7H15 | C6H4 | — | C5H11 |
| C4H9O | C6H4 | — | C3H7 |
| C4H9O | C6H4 | — | C5H11 |

TABLE 1-continued

| R¹ | A¹ | X¹ | R² |
|---|---|---|---|
| C₄H₉O | C₆H₄ | — | C₆H₁₃ |
| C₃H₇ | C₆H₄ | — | C₄H₉O |
| C₅H₁₁ | C₆H₄ | — | C₄H₉O |
| C₃H₇ | C₆H₄ | —CH₂CH₂— | C₇H₁₅ |
| C₅H₁₁ | C₆H₄ | —CH₂CH₂— | C₃H₇ |
| C₅H₁₁ | C₆H₄ | —CH₂CH₂— | C₅H₁₁ |
| C₅H₁₁ | C₆H₄ | —CH₂CH₂— | C₇H₁₅ |
| C₇H₁₅ | C₆H₄ | —CH₂CH₂— | C₃H₇ |
| C₄H₉O | C₆H₄ | —CH₂CH₂— | C₃H₇ |
| C₄H₉O | C₆H₄ | —CH₂CH₂— | C₅H₁₁ |
| C₅H₁₁ | C₆H₄ | —CH₂CH₂— | C₄H₉O |
| C₂H₅ | C₆H₁₀ | —CH₂CH₂— | C₃H₇ |
| C₃H₇ | C₆H₁₀ | —CH₂CH₂— | C₆H₁₃ |
| C₃H₇ | C₆H₁₀ | —CH₂CH₂— | C₇H₁₅ |
| C₅H₁₁ | C₆H₁₀ | —CH₂CH₂— | C₃H₇ |
| C₅H₁₁ | C₆H₁₀ | —CH₂CH₂— | C₄H₉ |
| C₅H₁₁ | C₆H₁₀ | —CH₂CH₂— | C₅H₁₁ |
| C₅H₁₁ | C₆H₁₀ | —CH₂CH₂— | C₇H₁₅ |
| C₇H₁₅ | C₆H₁₀ | —CH₂CH₂— | C₃H₇ |
| C₅H₁₁ | C₆H₁₀ | —CH₂CH₂— | C₄H₉O |
| C₃H₇ | C₆H₄ | — | C₅H₁₁—C₆H₄ |
| C₃H₇ | C₆H₄ | — | C₇H₁₅—C₆H₄ |
| C₅H₁₁ | C₆H₄ | — | C₃H₇—C₆H₄ |
| C₅H₁₁ | C₆H₄ | — | C₅H₁₁—C₆H₄ |
| C₅H₁₁ | C₆H₄ | — | C₇H₁₅—C₆H₄ |
| C₇H₁₅ | C₆H₄ | — | C₃H₇—C₆H₄ |
| C₇H₁₅ | C₆H₄ | — | C₅H₁₁—C₆H₄ |
| C₄H₉O | C₆H₄ | — | C₅H₁₁—C₆H₄ |
| C₅H₁₁ | C₆H₄ | — | C₄H₉O—C₆H₄ |
| C₃H₇—C₆H₄ | C₆H₄ | — | C₅H₁₁ |
| C₅H₁₁—C₆H₄ | C₆H₄ | — | C₃H₇ |
| C₅H₁₁—C₆H₄ | C₆H₄ | — | C₅H₁₁ |
| C₇H₁₅—C₆H₄ | C₆H₄ | — | C₃H₇ |
| C₄H₉O—C₆H₄ | C₆H₄ | — | C₅H₁₁ |
| C₅H₁₁—C₆H₄ | C₆H₄ | — | C₄H₉O |
| C₅H₁₁—C₆H₁₀CH₂CH₂— | C₆H₄ | — | C₃H₇ |
| C₅H₁₁—C₆H₁₀CH₂CH₂— | C₆H₄ | — | C₅H₁₁ |
| C₇H₁₅—C₆H₁₀CH₂CH₂— | C₆H₄ | — | C₃H₇ |

The compounds of formula I can be manufactured in accordance with the invention by (a) for the manufacture of the compounds of formula I in which R² signifies straight-chain $C_1$-$C_{12}$-alkyl or a group of formula II, oxidizing a compound of the formula

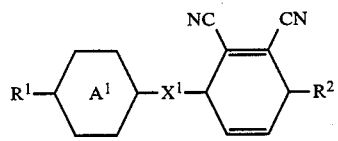

III wherein R² represents straight-chain $C_1$-$C_{12}$-alkyl or a group of formula II and R¹, X¹ and ring A¹ have the significances given above, or (b) for the manufacture of the compounds of formula I in which R² signifies straight-chain $C_1$-$C_{12}$-alkyl or a group of formula II, cleaving off hydrogen cyanide from a compound of the formula

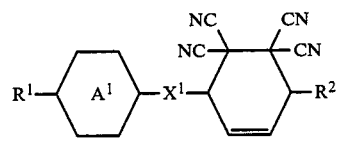

IV wherein R² represents straight-chain $C_1$-$C_{12}$-alkyl or a group of formula II and R¹, X¹ and ring A¹ have the significances given above, or (c) for the manufacture of the compounds of formula I in which R² signifies straight-chain $C_1$-$C_{12}$-alkoxy, reacting a compound of the formula

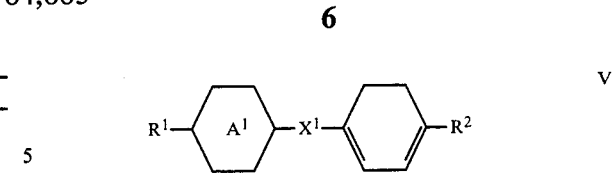

V wherein R² represents straight-chain $C_1$-$C_{12}$-alkoxy and R¹, X¹ and ring A¹ have the significances given above, with dicyanoacetylene and subsequently cleaving off ethylene.

These reactions can be carried out according to methods known per se. The oxidation of a compound of formula III is preferably carried out with 2,3-dichloro-5,6-dicyano-p-benzoquinone in dioxan or by catalytic dehydrogenation (preferably in the presence of a palladium catalyst). The cleavage of hydrogen cyanide from the compounds of formula IV is preferably carried out with caesium fluoride in dimethylformamide. The reaction of a compound of formula V with decyanoacetylene can be carried out according to the methods of the Diels-Alder reaction, preferably in an ether (e.g. tetrahydrofuran); the subsequent cleavage of ethylene from the Diels-Alder primary adduct obtained is preferably carried out by heating.

The compounds of formulae III-V above are novel and also form objects of the present invention.

The compounds of formula III can be obtained, for example, by reacting an aldehyde of the formula

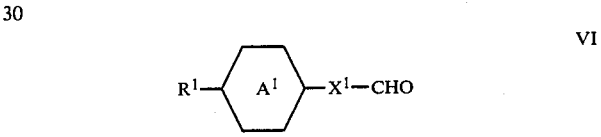

VI with a phosphonium salt of the formula

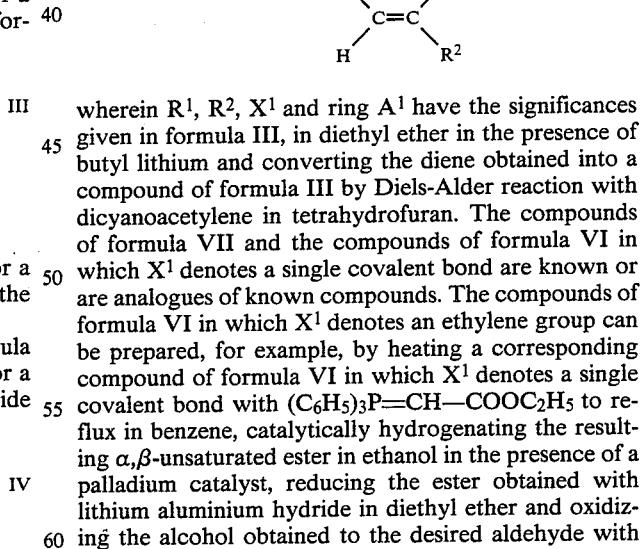

VII wherein R¹, R², X¹ and ring A¹ have the significances given in formula III, in diethyl ether in the presence of butyl lithium and converting the diene obtained into a compound of formula III by Diels-Alder reaction with dicyanoacetylene in tetrahydrofuran. The compounds of formula VII and the compounds of formula VI in which X¹ denotes a single covalent bond are known or are analogues of known compounds. The compounds of formula VI in which X¹ denotes an ethylene group can be prepared, for example, by heating a corresponding compound of formula VI in which X¹ denotes a single covalent bond with $(C_6H_5)_3P=CH$—$COOC_2H_5$ to reflux in benzene, catalytically hydrogenating the resulting α,β-unsaturated ester in ethanol in the presence of a palladium catalyst, reducing the ester obtained with lithium aluminium hydride in diethyl ether and oxidizing the alcohol obtained to the desired aldehyde with pyridinium chlorochromate in methylene chloride.

The compounds of formula IV can be prepared, for example, by reacting an aldehyde of formula VI with a phosphonium salt of formula VII in absolute diethyl ether in the presence of butyl lithium and converting the diene obtained into a compound of formula IV by Diels-Alder reaction with tetracyanoethylene in diethyl ether.

The compounds of formula V can be prepared, for example, by reducing a compound of the formula

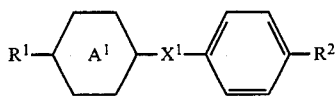

VIII wherein R² denotes straight-chain C₁-C₁₂-alkoxy and R¹, X¹ and ring A¹ have the significances given in formula I, with lithium and liquid ammonia (preferably in a diethyl ether/ethanol mixture). In this case there is generally obtained the 1,4-diene of a mixture of the 1,3-diene (a compound of formula V) and the 1,4-diene. The isomerization to the 1,3-diene can be carried out, for example, using 2,3-dichloromaleic anhydride. This is preferably carried out by using the product obtained in the above reaction directly for the subsequent Diels-Alder reaction [variant (c)] and adding 2,3-dichloromaleic anhydride to the reaction mixture. The compounds of formula VIII above are known or are analogues of known compounds.

The compounds provided by the invention can be used in the form of mixtures with liquid crystalline substances such as, for example, with substances from the classes of Schiff's bases, azobenzenes, azoxybenzenes, phenylbenzoates, cyclohexanecarboxylic acid phenyl esters and cyclohexyl esters, biphenyls, terphenyls, phenylcyclohexanes, cyclohexylbiphenyls, phenylpyrimidines, diphenylpyrimidines, cyclohexylphenylpyrimidines, phenyldioxanes and the like. Such substances are known to the person skilled in the art and many of them are, moreover, commercially available.

A preferred liquid crystalline substance is a liquid crystalline carrier material having a dielectric anisotropy of at most about +1.

The mixtures provided by the invention conveniently contain about 1-40 wt.% and preferably about 3-25 wt.% of compounds of formula I.

In principle, the compounds in accordance with the invention can be used in any liquid crystalline mixtures, for example, even in mixtures with positive dielectric anisotropy in order to adjust the dielectric anisotropies to the cell which is used. The compounds provided by the invention are, however, preferably used in mixtures with negative dielectric anisotropy or in mixtures which are suitable for the two-frequency control. Such mixtures can be manufactured in a manner known per se.

However, the mixtures provided by the invention for the two-frequency matrix addressing preferably consist of three components A, B and C, each of which contains one or more compounds, with component A having a viscosity of at most about 40 cp, a clearing point of at least about 40° C. and a dielectric anisotropy between about −2 and about +1, component B having a dielectric anisotropy below about −2 and containing at least one compound of formula I, and component C having a dielectric anisotropy above about +10, a clearing point of at least about 100° C. and a cross-over frequency in the total mixture of at most about 15 kHz at 20° C.

Such mixtures preferably consist of at least about 30 wt.% of component A, about 3-50 wt.% of component B and about 5-40 wt.% of component C and particularly of about 30-87 wt.% of component A, about 3-40 wt.% of component B and 10-30 wt.% of component C.

Compounds and mixtures having the above properties required for the components A, B and C are in principle known to the person skilled in the art. The total mixture must have nematic or cholesteric properties. Component A can be nematic or cholesteric and component C can be nematic, cholesteric or, provided that the total mixture is not smectic, also smectic. Components A and C must have at least monotropic liquid crystalline properties. However, there are preferred those mixtures in which at least component C is enantiotropic liquid crystalline and there are especially preferred those mixtures in which components A and C are enantiotropic liquid crystalline. Individual compounds in the mixtures provided by the invention and component B can, however, be liquid crystalline or non-liquid crystalline, but in the latter case care should be taken that the mesophase range of the total mixture is not restricted too severely.

Compounds and mixtures which are suitable as component A are to a large extent known and many of them are also commercially available. The following compounds or their mixtures are especially suitable:

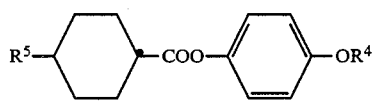

IX

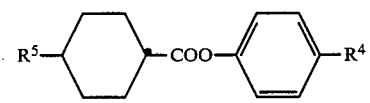

X

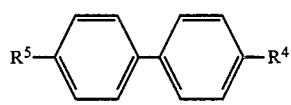

XI

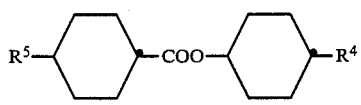

XII

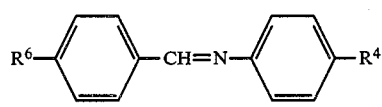

XIII

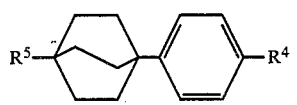

XIV

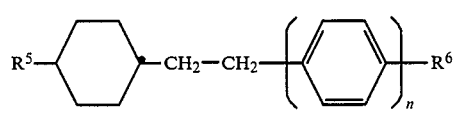

XV

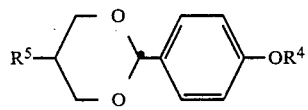

XVI

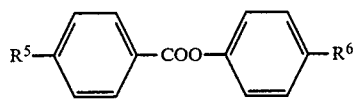 XVII
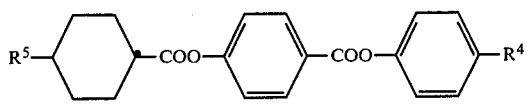 XVIII

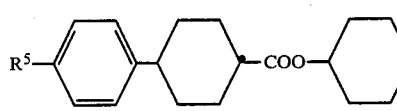 XIX
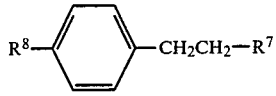 XX

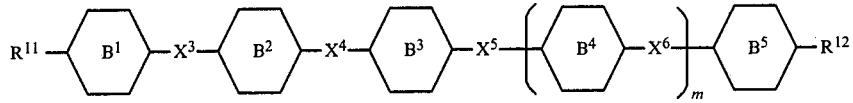 XXI wherein $R^4$ and $R^5$ signify straight-chain alkyl groups containing 1 to 8 carbon atoms, $R^6$ denotes a straight-chain alkyl or alkoxy group containing 1 to 8 carbon atoms and n is 1 or 2; $R^8$ represents trans-4-alkylcyclohexyl, 4'-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and $R^7$ represents trans-4-alkylcyclohexyl, or $R^8$ represents trans-4-alkylcyclohexyl and $R^7$ represents p-(trans-4-alkylcyclohexyl)phenyl, p-[2-trans-4-alkylcyclohexyl)ethyl]phenyl or 4'-(trans-4-alkylcyclohexyl)-4-biphenylyl, or $R^8$ represents p-alkylphenyl and $R^7$ represents p-[2-(trans-4-alkylcyclohexyl)ethyl]phenyl, and the alkyl groups in the substituents $R^7$ and $R^8$ denote straight-chain groups containing 1 to 7 carbon atoms; m stands for the number 0 or 1; one of the symbols $X^3$ and $X^4$ signifies an ester group —COO— or —OOC— and the remainder of the symbols $X^3$, $X^4$, $X^5$ and $X^6$ signify a single covalent bond, or one of these symbols also signifies the ethylene group —CH$_2$CH$_2$—; rings $B^1$ and $B^5$ denote a group of the formula

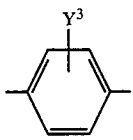 XXII or trans-1,4-cyclohexylene; rings $B^2$, $B^3$ and $B^4$ represents a group of formula XXII or, insofar as they are not linked with at least one of the other two of these rings by a single covalent bond, also trans-1,4-cyclohexylene; $Y^3$ signifies hydrogen or on a ring of formula XXII which is not linked with a further ring via a single covalent bond also fluorine, chlorine or methyl; and $R^{11}$ and $R^{12}$ denote a straight-chain alkyl containing 1 to 7 carbon atoms or on a ring of formula XXII also straight-chain alkoxy containing 1 to 7 carbon atoms. In an especially preferred embodiment the compounds of formulae IX–XII, XV, XX and XXI are used.

The compounds of formula I above have been found to be especially suitable compounds for component B. Other compounds suitable for component B which can be used in admixture with one or more compounds of formula I are, for example, the phenylpyridazines and diphenylpyridazines mentioned in Z. Chemie 17, 333 (1977), J. prakt, Chemie 151, 221 (1938), Z. Chemie 6, 467 (1966) and Mol. Cryst. Liq. Cryst. 25, 299 (1974) and the compounds which are described in German Offenlegungsschriften Nos. 2 933 563 and 2 937 700 and which have two lateral cyano groups. Especially suitable compounds which can be used in admixture with one or more compounds of formula I are, however, the dicyanophenyl esters of the formula

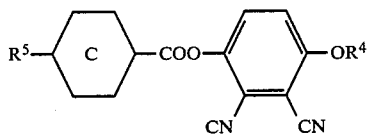 XXIII wherein $R^4$ and $R^5$ signify straight-chain alkyl groups containing 1 to 8 carbon atoms and ring C denotes p-phenylene or a trans-1,4-disubstituted cyclohexane ring, and especially the cyclohexylpyridazines of the formula

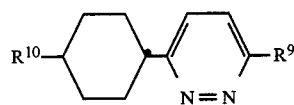 XXIV wherein $R^{10}$ signifies a straight-chain alkyl group containing 1 to 12 carbon atoms, $R^9$ represents an alkyl, 1-alkynyl, alkoxy, p-alkylphenyl, p-alkoxyphenyl or trans-4-alkylcyclohexyl group, the alkyl and alkoxy groups in $R^9$ are straight-chain groups containing 1 to 10 carbon atoms and the 1-alkynyl group in $R^2$ is a straight-chain group containing 2 to 10 carbon atoms. Under the aforementioned "dielectric anisotropy" of component B there is to be understood in the case of non-liquid crystalline components the extrapolated value (from liquid crystalline mixtures which contain this component) of the dielectric anisotropy at a temperature which lies 10° C. below the extrapolated (virtual) clearing point. For example, the compounds of formula I above have dielectric anisotropies of about −15 and the compounds of formula XXIV above have dielectric anisotropies of about −9.

For or as component C there are suitable, for example, compounds containing three or four p-phenylene or trans-1,4-cyclohexylene groups, a polar end group and optionally a lateral halogen or cyano substituent. Such compounds are partly known and are described, for example, in Mol. Cryst. Liq. Cryst. 63, 129 (1981) and German Offenlegungsschriften Nos. 2 736 772 (U.S. Pat. No. 4,149,413), 2 752 975 (U.S. Pat. No. 4,293,434) and 3 046 872 (U.S. Pat. No. 4,363,767).

Especially suitable compounds for component C are the compounds of the formula:

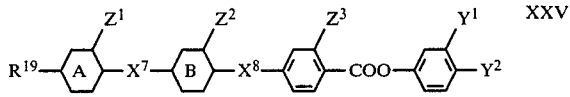

XXV wherein $X^8$ denotes a single covalent bond or the ester group —COO—; $X^7$ signifies a single covalent bond, the ester group —COO—, the ethylene group —CH$_2$CH$_2$— or, insofar as $X^8$ denotes the ester group —COO—, also p—C$_6$H$_4$—, p—C$_6$H$_4$—CH$_2$CH$_2$—, —CH$_2$CH$_2$—p—C$_6$H$_4$—, p—C$_6$H$_4$—COO— or —COO—p—C$_6$H$_4$—(p—C$_6$H$_4$— standing for p-phenylene); ring A stands for a benzene ring or for trans-1,4-cyclohexylene; ring B represents a benzene ring or, insofar as $X^8$ denotes the ester group —COO— and $X^7$ denotes a single covalent bond, the ester group —COO— or the ethylene group —CH$_2$CH$_2$—, also trans-1,4-cyclohexylene; the symbols $Z^1$, $Z^2$ and $Z^3$ signify hydrogen or on a benzene ring which is not linked directly with a further ring via a single covalent bond also halogen, cyano or methyl; $Y^2$ represents cyano, nitro or 2,2-dicyanovinyl or, insofar as $Y^1$ stands for hydrogen, also 2,2-dicyano-1-methylvinyl; $Y^1$ denotes halogen, cyano, C$_1$-C$_3$-alkyl or, insofar as $X^7$ has a benzene ring or an ester group or $Y^2$ stands for nitro or $Z^1$ and/or $Z^2$ are/is different from hydrogen, also hydrogen; and $R^{19}$ signifies C$_1$-C$_{12}$-alkyl or on a benzene ring also C$_1$-C$_{12}$-alkoxy, and the compounds of the formula:

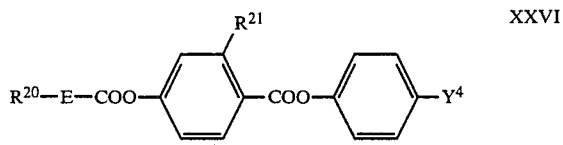

XXVI wherein $R^{21}$ denotes hydrogen, fluorine, chlorine, bromine or the cyano group, $Y^4$ represents 2,2-dicyanovinyl, 2,2-dicyano-1-methylvinyl or cyano, $R^{20}$ and E together signify p-$R^{20}$-phenyl, trans-4-$R^{20}$-cyclohexyl, 4'-$R^{20}$-4-biphenylyl, p-(trans-4-$R^{20}$-cyclohexyl)phenyl, p-(5-$R^{20}$-2-pyrimidinyl)phenyl, p-[2-(p'-$R^{20}$-phenyl)ethyl]phenyl, p-[2-(trans-4-$R^{20}$-cyclohexyl)ethyl]phenyl, trans-4-[2-(p-$R^{20}$-phenyl)ethyl]cyclohexyl or trans-4-[2-(trans-4-$R^{20}$-cyclohexyl)ethyl]cyclohexyl, and $R^{20}$ denotes a straight-chain alkyl group containing 1 to 12 carbon atoms or on a benzene ring also a straight-chain alkoxy group containing 1 to 12 carbon atoms. These compounds have large nematic mesophase ranges, low cross-over frequencies and large absolute dielectric anisotropies. The term "halogen" above stands for fluorine, chlorine or bromine, preferably for chlorine.

The mixtures provided by the invention with negative dielectric anisotropy conveniently contain, in addition to one or more compounds of formula I one or more additional compounds with negative and/or small positive anisotropy of the dielectric constants (compounds with positive dielectric anisotropy should in the use discussed herein be used in accordance with definition only in amounts which do not leave the anisotropy of the total mixture positive). The carrier material (remaining mixture without the compounds of formula I) conveniently has a dielectric anisotropy of at most about +1. Examples of preferred mixture components are the compounds named above in connection with components A and B and especially the compounds of formulae IX-XII, XV, XX, XXI, XXIII and XXIV.

The mixtures provided by the invention can also contain optically active compounds (e.g. optically active biphenyls) and/or dichroic colouring substances (e.g., azo, azoxy or anthraquinone colouring substances), in the case of the mixtures for the two-frequency addressing as ingredients of components A, B and C depending on properties. The amount of such compounds is determined by the solubility, the desired pitch, colour, extinction and the like. Preferably, the amount of optically active compounds amounts to at most about 4 wt.% and the amount of dichroic colouring substance amounts to at most about 10 wt.%, these percentages being based on the total mixture.

The manufacture of the liquid crystalline mixtures provided by the invention can be carried out in a manner known per se; for example, by heating a mixture of the ingredients to a temperature barely above the clearing point and subsequently cooling down.

The manufacture of an electro-optical device containing a mixture provided by the invention can also be carried out in a manner known per se; for example, by evacuating a suitable cell and introducing the mixture into the evacuated cell.

The compounds of formula XX are novel. They can be prepared as illustrated in the following Reaction Schemes 1 and 2 in which $R^{15}$ represents trans-4-alkylcyclohexyl, 4'-alkyl-4-biphenylyl, p-(trans-4-alkylcyclohexyl)phenyl or 2-(trans-4-alkylcyclohexyl)ethyl and $R^{16}$ represents trans-4-alkylcyclohexyl, or $R^{15}$ represents trans-4-alkylcyclohexyl and $R^{16}$ represents p-(trans-4-alkylcyclohexyl)phenyl, p-[2-(trans-4-alkylcyclohexyl)ethyl]phenyl or 4'-(trans-4-alkylcyclohexyl)-4-biphenylyl, or $R^{15}$ represents p-alkylphenyl and $R^{16}$ represents p-[2-(trans-4-alkylcyclohexyl)ethyl]phenyl, and $R^{13}$ and $R^{14}$ as well as the alkyl groups in the substituents $R^{15}$ and $R^{16}$ are straight-chain alkyl groups containing 1 to 7 carbon atoms.

Scheme 1

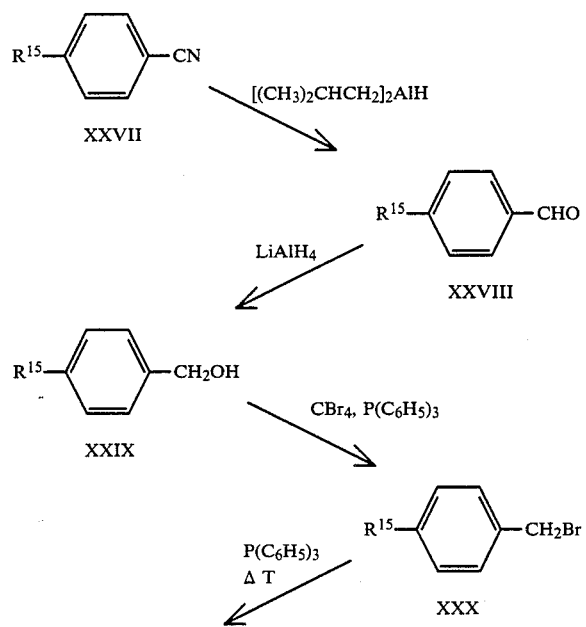

-continued
Scheme 1

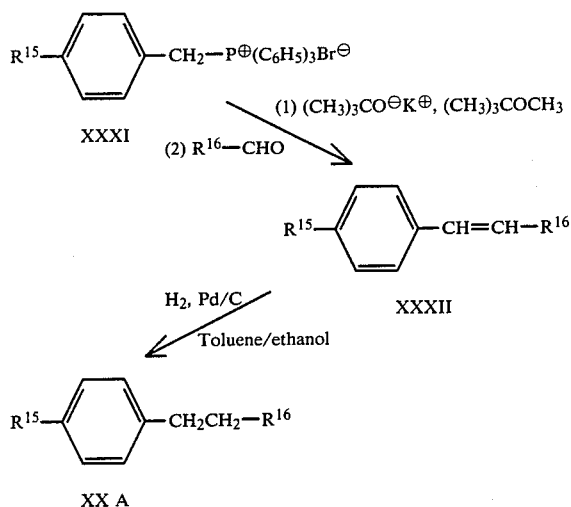

Scheme 2

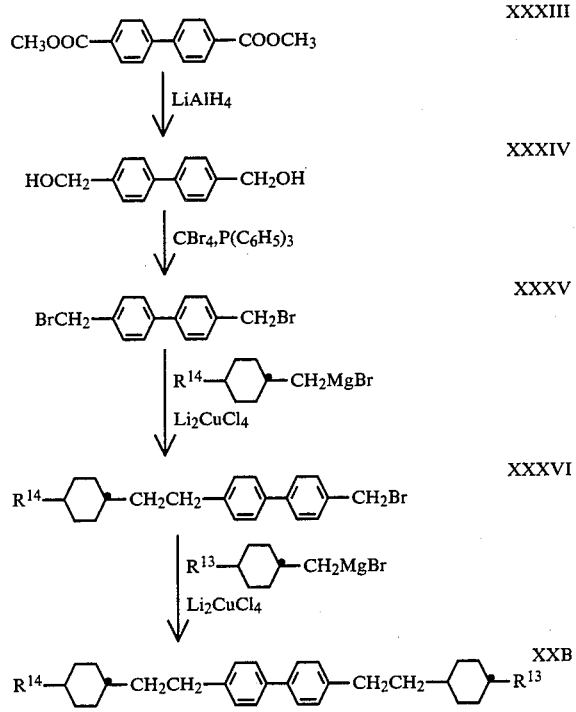

The compounds of formula $R^{16}$—CHO in Scheme 1 can be obtained in a simple manner from known compounds; for example, the trans-4-alkylcyclohexanecarboxaldehydes can be obtained by Rosenmund reduction of the corresponding acid chlorides and the remaining compounds can be obtained by reducing the corresponding cyano compounds.

By reacting the compound of formula XXXV with Grignard reagents in accordance with Scheme 2 there can be obtained compounds of formula XXXVI or directly compounds of formula XXB in which $R^{13}$ and $R^{14}$ have the same significance. When at least about 2 mol of Grignard reagent are used per mol of the compound of formula XXXV there is generally predominantly formed directly a compound of formula XXB.

The esters of formula XXI are also novel. They can be obtained according to esterification methods known per se (e.g. in an analogous manner to the preparation of the compounds of formula XXV described below). The starting materials required for the preparation of the esters of formula XXI are known or are analogues of known compounds and can be prepared according to known methods.

The compounds of formula XXIV are also novel. They can be prepared in a manner known per se by (a) for the preparation of the compounds of formula XXIV in which $R^9$ represents an alkyl, p-alkylphenyl, p-alkoxyphenyl or trans-4-alkylcyclohexyl group, subjecting a compound of the general formula

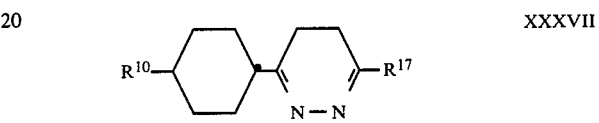

XXXVII wherein $R^{17}$ represents an alkyl, p-alkylphenyl, p-alkoxyphenyl or trans-4-alkylcyclohexyl group, the alkyl and alkoxy groups in $R^{17}$ are straight-chain groups containing 1 to 10 carbon atoms and $R^{10}$ has the above significance, or a tautomeric dihydropyridazine to oxidation (e.g. with 2,3-dichloro-5,6-dicyano-p-benzoquinone in dioxan, with sodium nitrite in glacial acetic acid and ethanol, with isopentyl nitrite in glacial acetic acid or preferably by catalytic dehydrogenation with palladium, platinum and the like), or (b) for the preparation of the compounds of formula XXIV in which $R^9$ represents an alkoxy group, reacting a compound of the general formula

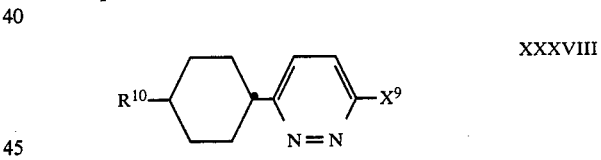

XXXVIII wherein $X^9$ denotes chlorine or bromine and $R^{10}$ has the above significance, with an alkali metal alcoholate (e.g. sodium methylate), or (c) for the preparation of the compounds of formula XXIV in which $R^9$ represents the ethynyl group, reacting a compound of the general formula

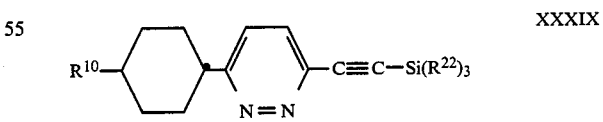

XXXIX wherein $R^{22}$ denotes an alkyl group containing 1 to 5 carbon atoms and $R^{10}$ has the above significance, with a base (e.g. potassium hydroxide, sodium hydroxide or butyl lithium), or (d) for the preparation of the compounds of formula XXIV in which $R^9$ represents a 1-alkynyl group containing 3 to 10 carbon atoms, converting a compound of the general formula

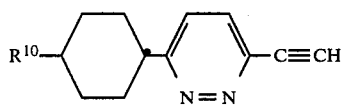 XL wherein $R^{10}$ has the above significance, with a base (e.g. butyl lithium, methyl lithium, sodium amide or lithium diisopropylamide) into the corresponding ethynylide and alkylating the ethynylide with an alkyl bromide or alkyl iodide.

The compounds of formula XXXVII can rearrange to tautomeric compounds by migration of the double bonds in the dihydropyridazine ring. Such rearrangements can be brought about, for example, by the presence of a trace of acid or base. Since the tautomeric dihydropyridazines can, however also be oxidized under the above conditions to compounds of formula XXIV, not only a compound of formula XXXVII but also a tautomeric dihydropyridazine or a mixture of such compounds can be reacted in accordance with variant (a).

The starting materials of formulae XXXVII and XXXVIII are novel. They can be prepared as illustrated in the following Reaction Schemes 3–6 in which $R^{10}$, $R^{17}$ and $X^9$ have the above significances and $R^{18}$ represents a straight-chain alkyl or alkoxy group containing 1 to 10 carbon atoms.

Scheme 3

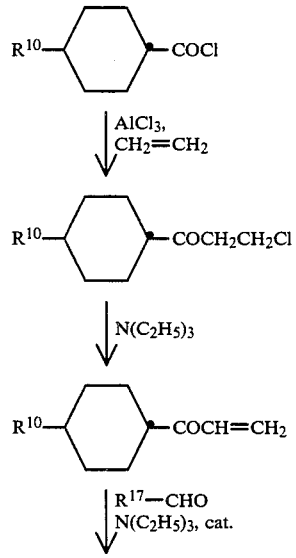

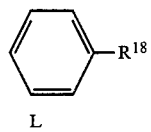

L

Scheme 3 -continued

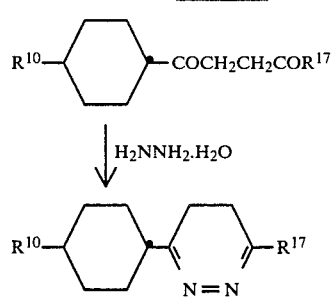

Scheme 4

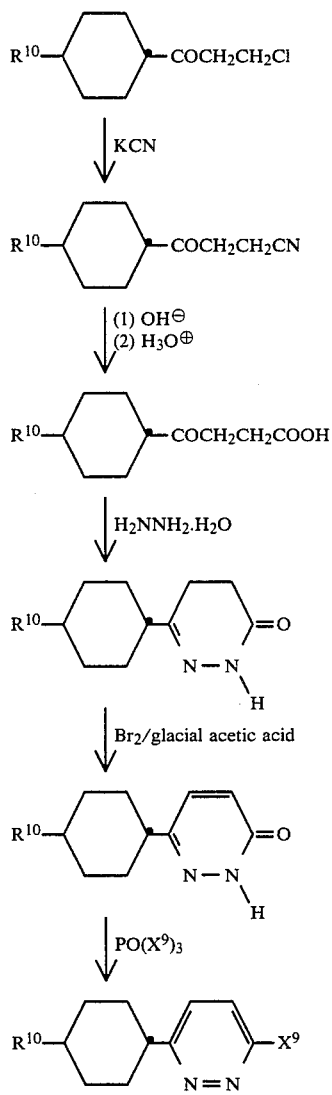

Scheme 5

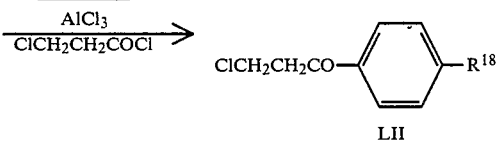

LII

4,704,005
Scheme 5
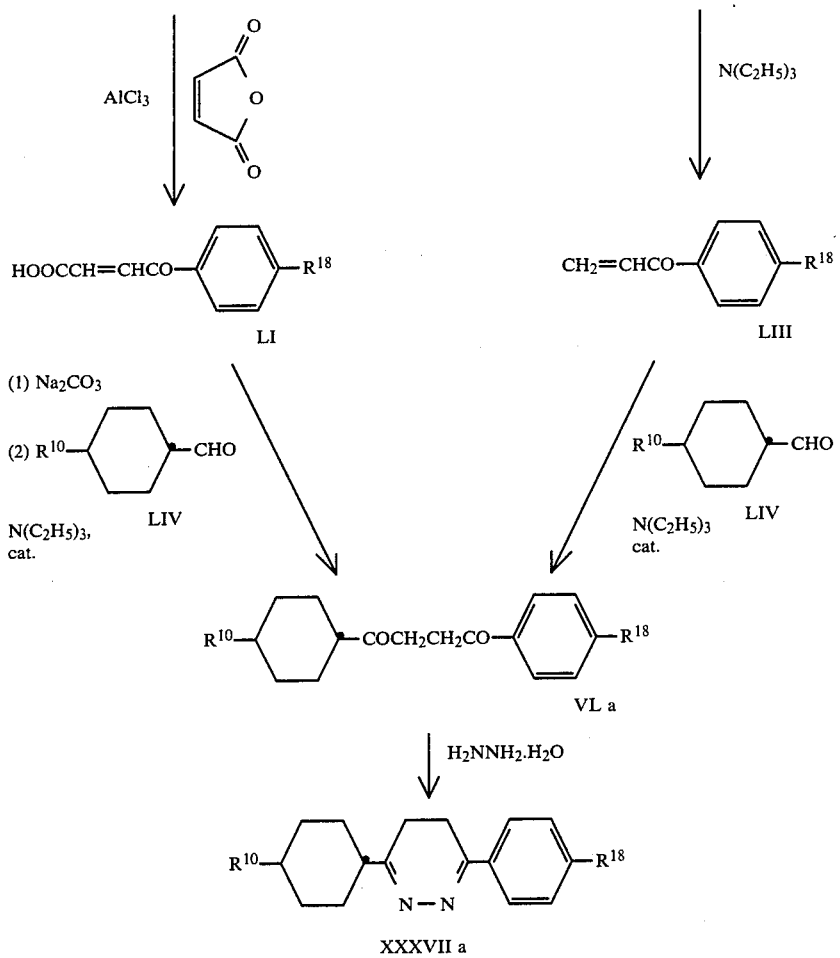
Scheme 6
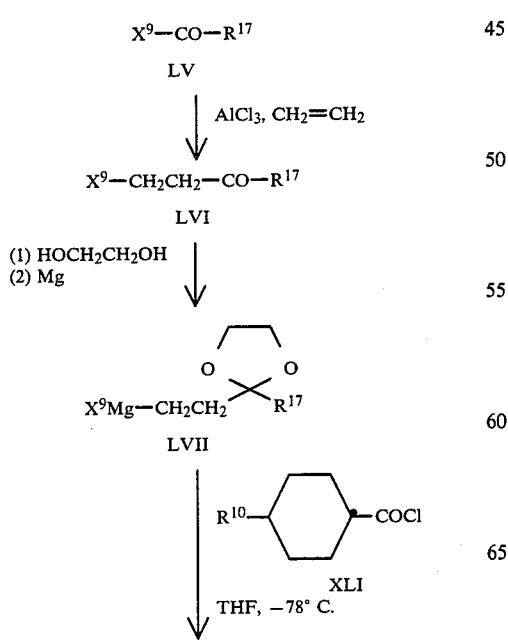
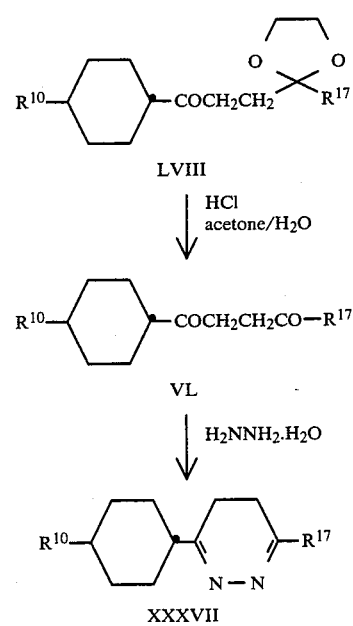

The starting materials of formulae XLI, XXXXIV, L, LIV and LV are known or are analogues of known compounds and can be prepared in a known manner. For example, the aldehydes of formula LIV can be prepared by Rosenmund reduction of the acid chlorides of formula XLI.

The addition of an aldehyde to a compound of formula XLIII, LI or LIII can be carried out according to the method of Stetter (Chem. Ber. 114 (1981) 581) in the presence of a 1,3-thiazolium salt catalyst. 3-Benzyl-5-(2-hydroxyethyl)-4-methyl-1,3-thiazolium chloride is the preferred catalyst for the addition of an aldehyde of formula LIV or of an aldehyde of formula XXXXIV in which $R^{17}$ signifies alkyl or trans-4-alkylcyclohexyl and 3,4-dimethyl-5-(2-hydroxyethyl)-1,3-thiazolium iodide is the preferred catalyst for the addition of an aldehyde of formula XXXXIV in which $R^{17}$ signifies p-alkylphenyl or p-alkoxyphenyl.

The coupling of a compound of formula LVII with a compound of formula XLI can be carried out according to the method of T. Sato et al., Bull. Chem. Soc. Japan 54 (1981) 505.

The compounds of formula XXXIX are also novel. They can be obtained in a manner known per se by reacting a compound of formula XXXVIII with an ethynyl-trialkylsilane in the presence of triethylamine, bis-(triphenylphosphine)palladium (II) dichloride and copper (I) iodide.

The compounds of formula XXV are also novel. They can be prepared in a manner known per se by esterifying the acid chloride of a compound of the formula

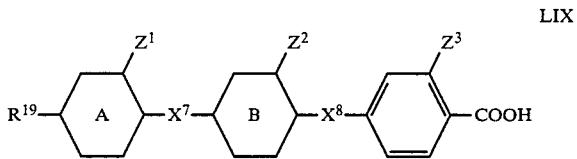

LIX wherein $R^{19}$, A, B, $X^7$, $X^8$, $Z^1$, $Z^2$ and $Z^3$ have the significances given in formula XXV, with a phenol of the formula

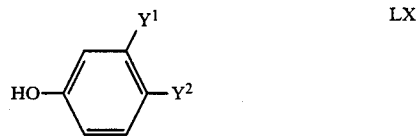

LX wherein $Y^1$ and $Y^2$ have the significance given in formula XXV, and, if desired, reacting a compound of formula XXV obtained in which $Z^1$, $Z^2$ or $Z^3$ signifies bromine with copper (I) cyanide, sodium cyanide or potassium cyanide.

The compounds of formula LX in which $Y^2$ signifies 2,2-dicyanovinyl can be prepared, for example, by converting 3-$Y^1$-anisole into 4-methoxy-2-$Y^1$-benzaldehyde by a Vilsmeier reaction with dimethylformamide in the presence of phosphorus oxychloride, then hydrolyzing the methoxy group (e.g. by heating under reflux with pyridinium chloride and subsequent fractional distillation) and finally converting the 4-hydroxy-2-$Y^1$-benzaldehyde obtained into the compound of formula IV in which $Y^2$ signifies 2,2-dicyanovinyl by a Knoevenagel condensation with malononitrile (e.g. in the presence of catalytic amounts of glacial acetic acid and sodium acetate in boiling toluene). The remaining compounds of formula LX are known or are analogues of known compounds.

The compounds of formula LIX are also known or are analogues of known compounds and can be prepared according to known methods.

The compounds of formula LIX in which $X^8$ denotes the ester group —COO— can be prepared, for example, by esterifying a compound of the formula

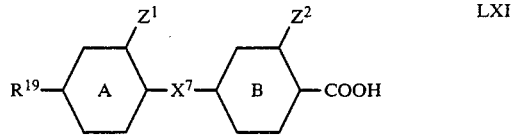

LXI wherein $X^7$, $R^{19}$, A, B, $Z^1$ and $Z^2$ have the significances given in formula XXV, with 4-hydroxy-2-$Z^3$-benzaldehyde in methylene chloride in the presence of dicyclohexylcarbodiimide and 4-(dimethylamino)pyridine and converting the resulting aldehyde into the corresponding acid of formula LIX by Jones' oxidation with chromic acid and sulphuric acid.

In the preparation of the acids of formula LIX in which $X^7$ signifies —CH$_2$CH$_2$—, p—C$_6$H$_4$—CH$_2$CH$_2$— or —CH$_2$CH$_2$—p—C$_6$H$_4$— and $X^8$ signifies a single covalent bond and of the acids of formula LXI in which $X^7$ signifies —CH$_2$CH$_2$—, p—C$_6$H$_4$—CH$_2$CH$_2$— or —CH$_2$—CH$_2$—p—C$_6$H$_4$—, the linkage of rings A and B is conveniently carried out by a Fouquet-Schlosser reaction of by a Wittig reaction. For example, 4-(bromomethyl)-2-$Z^2$-benzonitrile, 4'-(bromomethyl)-4-biphenylcarbonitrile or trans-4-(tosyloxymethyl)cyclohexanecarbonitrile can be reacted with (4-$R^{19}$-2-$Z^1$-phenyl)methylmagnesium bromide or (trans-4-$R^{19}$-cyclohexyl)methylmagnesium bromide in the presence of dilithium tetrachlorocuprate and the nitrile obtained can be hydrolyzed to the desired acid. Further, for example, 4-$R^{19}$-2-$Z^1$-benzaldehyde or trans-4-$R^{19}$-cyclohexanecarboxaldehyde can be reacted with (4-methoxycarbonyl-3-$Z^2$-phenyl)methyl-triphenylphosphonium bromide ($Z^1$ and $Z^2$ signifying hydrogen, fluorine, cyano or methyl) in the presence of a base (e.g. sodium methylate), then the double bond can be catalytically hydrogenated and finally the ester group can be saponified.

The starting materials required for these reactions are known or can be prepared according to methods known per se. For example, 4-alkoxy-2-$Z^1$-acetophenone can be converted by haloform degradation into 4-alkoxy-2-$Z^1$-benzoic acid and this can be converted into 4-alkoxy-1-(bromomethyl)-2-$Z^1$-benzene by reduction with lithium aluminium hydride and bromination (e.g. with tetrabromomethane and triphenylphosphine). From methyl 2,4-dimethylbenzoate there can be obtained, for example, by reaction with N-bromosuccinimide and subsequent isomer separation methyl 4-(bromomethyl)-2-methylbenzoate which can be converted into methyl 4-formyl-2-methylbenzoate in an analogous manner to Org. Synth. Coll. V, 825; the methyl 4-alkyl-2-methylbenzoate obtained after reaction with alkyltriphenylphosphonium bromide and base and subsequent catalytic hydrogenation of the double bond can be saponified with sodium hydroxide to the acid or reduced with lithium aluminium hydride to the alcohol which finally can be converted with hydrogen bromide into 4-alkyl-1-(bromomethyl)-2-methylbenzene or with manganese dioxide into the 4-alkyl-2-methylbenzaldehyde. 1-Alkyl-3-fluorobenzene can be converted, for example, into 4-alkyl-2-fluorobenzoic acid by reaction with butyl lithium and carbon dioxide and subsequent hydrolysis and 1-alkyl-3-chlorobenzene or 1-alkyl-3-bromobenzene can be converted into 4-alkyl-2-(chloro or bromo)benzoic acid by Friedel-Crafts acylation with acetyl chloride in the presence of aluminium trichloride and subsequent oxidation with sodium hypobromite; the acids obtained can then be converted with lithium aluminium hydride into the alcohols and these can be converted into the bromides with hydrogen bromide or into the aldehydes with manganese dioxide. Further, for example, 4-methyl-2-$Z^1$-benzoic acid can be reacted in sequence with thionyl chloride, ammonia and benzenesulphonyl chloride and the 4-methyl-2-$Z^1$-benzonitrile obtained can be converted into 4-(bromomethyl)-2-$Z^1$-benzonitrile with N-bromosuccinimide.

The compounds of formula XXVI are in part also novel compounds. They can be prepared by esterification in an analogous manner to the compounds of formula XXV. The acids required for the preparation of the compounds of formula XXVI can be obtained as illustrated in Reaction Scheme 7 in which $R^{20}$, $R^{21}$ and E have the significances given in formula XXVI above:

Scheme 7

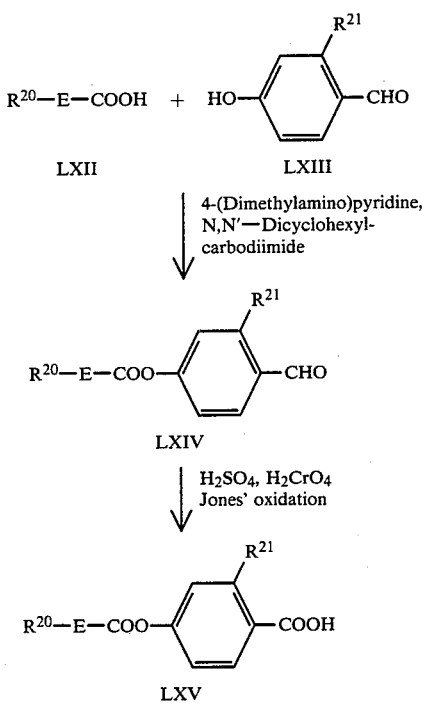

The compounds of formulae LXII and LXIII are known or can be prepared according to methods known per se.

The invention is also concerned with all novel compounds, mixtures, processes, uses and devices as herein described.

In the following Mixtures, Examples 1 through 8, which are examples of preferred inventive mixtures, $\eta$ denotes the viscosity (bulk viscosity), $f_c$ signifies the cross-over frequency, $\Delta\epsilon_l$ denotes the low frequency ("static") dielectric anisotropy and $\Delta\epsilon_h$ denotes the high frequency dielectric anisotropy measured at 22° C. Mixture Examples 1–6 have negative dielectric anisotropy and Mixture Examples 7 and 8 are suitable for the two-frequency addressing. Unless indicated otherwise, the mixture and chemical examples were carried out as written.

Mixture 1

11.8 wt.% of trans-4-butylcyclohexanecarboxylic acid p-ethoxyphenyl ester,
16.6 wt.% trans-4-butylcyclohexanecarboxylic acid p-pentyloxyphenyl ester,
10.7 wt.% trans-4-pentylcyclohexanecarboxylic acid p-methoxyphenyl ester,
12.8 wt.% trans-4-pentylcyclohexanecarboxylic acid p-propyloxypheyl ester,
7.3 wt.% of 4-ethoxy-1-[2-(trans-4-pentylcyclohexyl)ethyl]benzene,
3.5 wt.% 3-propyl-6-(trans-4-ethylcyclohexyl)pyridazine,
8.3 wt.% 3-propyl-6-(trans-4-pentylcyclohexyl)pyridazine,
5.3 wt.% 3-propyl-6-(trans-4-heptylcyclohexyl)pyridazine,
10.7 wt.% 3-pentyl-6-(trans-4-pentylcyclohexyl)pyridazine,
8.7 wt.% 4'-(trans-4-pentylcyclohexyl)-4-[2-(trans-4-butylcyclohexyl)ethyl]biphenyl,
4.3 wt.% 2,3-dicyano-1-[2-(trans-4-pentylcyclohexyl)ethyl]-4-propylbenzene;
m.p. −12° C., cl.p. 60° C., nematic; $\eta=40$ cp, $\Delta\epsilon_l = -5.07$.

Mixture 2

5.6 wt.% of trans-4-butylcyclohexanecarboxylic acid p-ethoxyphenyl ester,
5.1 wt.% trans-4-pentylcyclohexanecarboxylic acid p-methoxyphenyl ester,
9.8 wt.% trans-4-pentylcyclohexanecarboxylic acid p-propyloxyphenyl ester,
12.7 wt.% 4-ethoxy-1-[2-(trans-4-propylcyclohexyl)ethyl]benzene,
14.6 wt.% 4-ethoxy-1-[2-(trans-4-pentylcyclohexyl)ethyl]benzene,
10.3 wt.% 1-[2-(trans-4-butylcyclohexyl)ethyl]-4-(trans-4-pentylcyclohexyl)benzene,
3.4 wt.% 3-propyl-6-(trans-4-ethylcyclohexyl)pyridazine,
8.2 wt.% of 3-propyl-6-(trans-4-pentylcyclohexyl)pyridazine,
5.2 wt.% 3-propyl-6-(trans-4-heptylcyclohexyl)pyridazine,
10.5 wt.% 3-pentyl-6-(trans-4-pentylcyclohexyl)pyridazine,
10.3 wt.% 4'-(trans-4-pentylcyclohexyl)-4-[2-(trans-4-butylcyclohexyl)ethyl]biphenyl,
4.3 wt.% 2,3-dicyano-1-[2-(trans-4-pentylcyclohexyl)ethyl]-4-propylbenzene;
m.p. <0° C., cl.p. 57.8° C., nematic; $\eta=31.9$ cp, $\Delta\epsilon_l = -4.69$.

Mixture 3

16.5 wt.% of trans-4-butylcyclohexanecarboxylic acid p-ethoxyphenyl ester,
23.3 wt.% trans-4-butylcyclohexanecarboxylic acid p-pentyloxyphenyl ester, 15.0 wt.% trans-4-pentylcyclohexanecarboxylic acid p-methoxyphenyl ester,
18.0 wt.% trans-4-pentylcyclohexanecarboxylic acid p-propyloxyphenyl ester,
10.2 wt.% 4-ethoxy-1-[2-(trans-4-pentylcyclohexyl)ethyl]benzene,
7.0 wt.% 2,3-dicyano-1-[2-(trans-4-pentylcyclohexyl)ethyl]-4-propylbenzene,
10.0 wt.% 2,3-dicyano-1-[2-(trans-4-pentylcyclohexyl)ethyl]-4-butylbenzene;
m.p. <0° C., cl.p. 49° C., nematic; $\eta = 45$ cp, $\Delta\epsilon_1 = -4.01$.

Mixture 4

10.9 wt.% of trans-4-butylcyclohexanecarboxylic acid p-ethoxyphenyl ester,
15.4 wt.% trans-4-butylcyclohexanecarboxylic acid p-pentyloxyphenyl ester,
9.9 wt.% trans-4-pentylcyclohexanecarboxylic acid p-methoxyphenyl ester,
11.9 wt.% trans-4-pentylcyclohexanecarboxylic acid p-propyloxyphenyl ester,
6.7 wt.% 4-ethoxy-1-[2-(trans-4-pentylcyclohexyl)ethyl]benzene,
9.6 wt.% 1-[2-(trans-4-butylcyclohexyl)ethyl]-4-(trans-4-pentylcyclohexyl)benzene,
7.7 wt.% 4-[2-(trans-4-butylcyclohexyl)ethyl]-4'-(trans-4-pentylcyclohexyl)-1,1'-ethylenedibenzene,
3.9 wt.% 4-[2-(trans-4-butylcyclohexyl)ethyl]-4'-(trans-4-pentylcyclohexyl)biphenyl,
9.6 wt.% 2,3-dicyano-1-[2-(trans-4-pentylcyclohexyl)ethyl]-4-propylbenzene,
14.4 wt.% 2,3-dicyano-1-[2-(trans-4-pentylcyclohexyl)ethyl]-4-butylbenzene;
m.p. <0° C., cl.p. 61.5° C., nematic; $\eta = 67.9$ cp, $\Delta\epsilon_1 = -5.22$.

Mixture 5

12.3 wt.% of trans-4-butylcyclohexanecarboxylic acid p-ethoxyphenyl ester,
17.4 wt.% of trans-4-butylcyclohexanecarboxylic acid p-pentyloxyphenyl ester,
11.2 wt.% trans-4-pentylcyclohexanecarboxylic acid p-methoxyphenyl ester,
13.5 wt.% trans-4-pentylcyclohexanecarboxylic acid p-propyloxyphenyl ester,
7.6 wt.% 4-ethoxy-1-[2-(trans-4-pentylcyclohexyl)ethyl]benzene,
10.0 wt.% 1-[2-(trans-4-butylcyclohexyl)ethyl]-4-(trans-4-pentylcyclohexyl)benzene,
8.0 wt.% 4-[2-(trans-4-butylcyclohexyl)ethyl]-4'-(trans-4-pentylcyclohexyl)-1,1'-ethylenedibenzene,
8.0 wt.% 2,3-dicyano-1-[2-(trans-4-pentylcyclohexyl)ethyl]-4-propylbenzene,
12.0 wt.% 2,3-dicyano-1-[2-(trans-4-pentylcyclohexyl)ethyl]-4-butylbenzene;
m.p. <0° C., cl.p. 65.4° C., nematic; $\eta = 47$ cp, $\Delta\epsilon_1 = -3.71$.

Mixture 6

11.58 wt.% of trans-4-butylcyclohexanecarboxylic acid p-ethoxyphenyl ester,
16.31 wt.% trans-4-butylcyclohexanecarboxylic acid p-pentyloxyphenyl ester,
10.47 wt.% trans-4-pentylcyclohexanecarboxylic acid p-methoxyphenyl ester,
12.64 wt.% trans-4-pentylcyclohexanecarboxylic acid p-propyloxyphenyl ester,
7.12 wt.% of 4-ethoxy-1-[2-(trans-4-pentylcyclohexyl)ethyl]benzene,
10.26 wt.% 4-[2-(trans-4-butylcyclohexyl)ethyl]-4'-(trans-4-pentylcyclohexyl)biphenyl,
3.38 wt.% 3-propyl-6-(trans-4-ethylcyclohexyl)pyridazine,
8.21 wt.% 3-propyl-6-(trans-4-pentylcyclohexyl)pyridazine,
10.51 wt.% 3-pentyl-6-(trans-4-pentylcyclohexyl)pyridazine,
5.25 wt.% 3-propyl-6-(trans-4-heptylcyclohexyl)pyridazine,
4.27 wt.% 2,3-dicyano-1-[2-(trans-4-pentylcyclohexyl)ethyl]-4-propylbenzene;
m.p. <−10° C., cl.p. 61.5° C., nematic; $\eta = 42.8$ cp, $\Delta\epsilon_1 = -5.05$.

Mixture 7

12.9 wt.% of trans-4-butylcyclohexanecarboxylic acid p-ethoxyphenyl ester,
18.3 wt.% trans-4-butylcyclohexanecarboxylic acid p-pentyloxyphenyl ester,
11.7 wt.% trans-4-pentylcyclohexanecarboxylic acid p-methoxyphenyl ester,
14.1 wt.% trans-4-pentylcyclohexanecarboxylic acid p-propyloxyphenyl ester,
8.0 wt.% 4-ethoxy-1-[2-(trans-4-pentylcyclohexyl)ethyl]benzene,
9.0 wt.% of 4'-(trans-4-pentylcyclohexyl)-4-biphenylcarboxylic acid 3-chloro-4-[(3-chloro-4-nitrophenoxy)carbonyl]phenyl ester,
9.0 wt.% 4'-(trans-4-heptylcyclohexyl)-4-biphenylcarboxylic acid 3-chloro-4-[(3-chloro-4-nitrophenoxy)carbonylphenyl]ester,
7.0 wt.% 2,3-dicyano-1-[2-(trans-4-pentylcyclohexyl)ethyl]-4-propylbenzene,
10.0 wt.% 2,3-dicyano-1-[2-(trans-4-pentylcyclohexyl)ethyl]-4-butylbenzene;
m.p. <0° C., cl.p. 76.6° C., nematic; $f_c = 440$ Hz, $\Delta\epsilon_1 = +5.2$, $\Delta\epsilon_h = -5.0$.

Mixture 8

6.8 wt.% of trans-4-butylcyclohexanecarboxylic acid p-ethoxyphenyl ester,
9.7 wt.% trans-4-butylcyclohexanecarboxylic acid p-pentyloxyphenyl ester,
6.3 wt.% trans-4-pentylcyclohexanecarboxylic acid p-methoxyphenyl ester,
11.2 wt.% trans-4-pentylcyclohexanecarboxylic acid p-propyloxyphenyl ester,
16.4 wt.% 4-ethoxy-1-[2-(trans-4-pentylcyclohexyl)ethyl]benzene,
11.1 wt.% 1-[2-(trans-4-butylcyclohexyl)ethyl]-4-(trans-4-pentylcyclohexyl)benzene,
4.5 wt.% 4'-hexyl-4-biphenylcarboxylic acid 3-chloro-4-[(3-chloro-4-cyanophenoxy)carbonyl]phenyl ester,
4.5 wt.% of 4'-heptyl-4-biphenylcarboxylic acid 3-chloro-4-[(3-chloro-4-cyanophenoxy)carbonyl]phenyl ester,
4.5 wt.% 4'-hexyl-4-biphenylcarboxylic acid 3-chloro-4-[(3-chloro-4-nitrophenoxy)carbonyl]phenyl ester,
4.5 wt.% 4'-heptyl-4-biphenylcarboxylic acid 3-chloro-4-[(3-chloro-4-nitrophenoxy)carbonyl]phenyl ester,
8.2 wt.% 2,3-dicyano-1-[2-(trans-4-pentylcyclohexyl)ethyl]-4-propylbenzene,
12.3 wt.% 2,3-dicyano-1-[2-(trans-4-pentylcyclohexyl)ethyl]-4-butylbenzene;

m.p. <0° C., cl.p. 65.5° C., nematic; $f_c=3.6$ kHz, $\Delta\epsilon_l=+6.11$, $\Delta\epsilon_h=-5.40$.

The following chemical Examples illustrate the manufacture of the compounds provided by the invention, and the preparation of certain starting materials. Unless otherwise stated, percentages and ratios relating to solvent mixtures are expressed in volume, purity data determined by gas chromatography are expressed in area % and the remaining percentages and ratios are expressed in weight. Temperatures are in degrees Celsius (°C.), normal pressure is about 1 atmosphere and room temperature is about 23° C. The petroleum ether is a well-known mixture of low-boiling hydrocarbons. Unless indicated otherwise, the Examples were carried out as written.

EXAMPLE 1

A solution (50 ml) of 19.5 g of 4-butyloxy-1-[2-(trans-4-pentylcyclohexyl)ethyl]-1,4-cyclohexadiene in tetrahydrofuran was placed in a round flask under nitrogen gasification and treated while stirring with a solution of 50 mg of 2,3-dichloromaleic anhydride and 4.1 g of dicyanoacetylene in 50 ml of tetrahydrofuran. The mixture was stirred at room temperature for 24 hours and then evaporated in vacuo. The resulting dark brown oil (30.7 g) was chromatographed on silica gel using methylene chloride and methylene chloride/1% acetone as the eluent. This procedure yielded 15.7 g of dark brown oil which was then heated continuously up to 125° C. within 1 hour. The residue (15.2 g) was chromatographed on silica gel using toluene as the eluent. This procedure isolated 11.7 g of a brown solid residue which was dissolved in diethyl ether, treated with active carbon and filtered. After repeated recrystallization (from diethyl ether/hexane, acetone/isopropanol and isopropanol) and chromatographic working-up of the mother liquors, 5.4 g of pure 4-butyloxy-2,3-dicyano-1-[2-(trans-4-pentylcyclohexyl)ethyl]benzene were finally obtained; m.p. 145.1° C.

The 4-butyloxy-1-[2-(trans-4-pentylcyclohexyl)ethyl]-1,4-cyclohexadiene used as the starting material was prepared as follows:

1306 ml of liquid ammonia were placed in a sulphonation flask and then a solution of 38.4 g of 4-butyloxy-1-[2-(trans-4-pentylcyclohexyl)ethyl]benzene in 1.1 l of diethyl ether was added dropwise within 40 minutes while cooling. 23.3 g of lithium wire were subsequently added within 35 minutes and the mixture was stirred for 2 hours. 420 ml of ethanol were then added dropwise to the mixture within 70 minutes and the ammonia was allowed to evaporate overnight under nitrogen. The mixture was cooled to 10° C. and 1.5 l of water were then added dropwise within 35 minutes in such a manner that the temperature did not rise above 10° C. The mixture was extracted three times with 0.5 l of diethyl ether each time. The organic phases were washed twice with 0.5 l of water each time, dried over potassium carbonate, filtered and concentrated, there being obtained 39.0 g of 4-butyloxy-1-[2-(trans-4-pentylcyclohexyl)ethyl]-1,4-cyclohexadiene as a colourless crystallizing oil.

EXAMPLE 2

7.4 g of 1,2-dicyano-3-[2-(trans-4-pentylcyclohexyl)ethyl]-6-propyl-1,4-cyclohexadiene were dissolved in 100 ml of dioxan in a round flask in an oil-bath (120° C.), the solution was treated with 4.76 g of 2,3-dichloro-5,6-dicyano-p-benzoquinone and the mixture was boiled under reflux for 2.5 hours. The mixture was subsequently cooled to room temperature and the resulting precipitate was filtered off under suction and rinsed with dioxan and diethyl ether. The filtrate was concentrated in vacuo. The brown solid residue (9.9 g) was chromatographed on silica gel using toluene/hexane (volume ratio 1:1) and toluene as the eluent. The isolated crude product (7.0 g) was recrystallized several times (from hexane and isopropanol), there being finally obtained 2.3 g of pure 2,3-dicyano-1-[2-(trans-4-pentylcyclohexyl)ethyl]-4-propylbenzene; m.p. 83.6° C.

The 1,2-dicyano-3-[2-(trans-4-pentylcyclohexyl)ethyl]-6-propyl-1,4-cyclohexadiene used as the starting material was prepared as follows:

(a) 20.4 g of trans-4-pentylcyclohexanecarboxaldehyde were dissolved in 500 ml of benzene in a round flask under nitrogen and treated with 49.5 g of the phosphorane $(C_6H_5)_3P=CHCOOC_2H_5$ [Helv. Chim. Acta 40, 1242 (1957)]. The mixture was heated to boiling, boiled at reflux for 6 hours under nitrogen and left to stand overnight. After concentration in vacuo, there were obtained 73.2 g of yellowish semi-solid residue. Chromatography of the residue on silica gel using toluene/hexane (volume ratio 1:1) and toluene finally gave 27.7 g of ethyl β-(trans-4-pentylcyclohexyl)acrylate as an almost colourless oil; b.p. 104°-116° C./0.07 mmHg.

(b) 41.6 g of ethyl β-(trans-4-pentylcyclohexyl)acrylate were dissolved in 368 ml of ethanol, treated with 7.4 g of palladium/carbon (5%) and hydrogenated at room temperature and under normal pressure until the hydrogen uptake came to a standstill (hydrogen uptake 0.167 mol). The mixture was gassed with nitrogen and filtered (rinsing with ethanol and methylene chloride). Concentration of the filtrate in vacuo gave 38.4 g of ethyl β-(trans-4-pentylcyclohexyl)propionate as a colourless oil which was distilled in a high vacuum; b.p. 113°-121° C./0.05-0.06 mmHg.

(c) 250 ml of absolute diethyl ether were placed in a sulphonation flask under nitrogen gasification and treated cautiously with 3.9 g of lithium aluminium hydride. A solution of 46.9 g of ethyl β-(trans-4-pentylcyclohexyl)propionate in 200 ml of absolute diethyl ether was added dropwise thereto within 50 minutes. A further 250 ml of absolute diethyl ether were then added thereto and the mixture was stirred overnight. Subsequently, there were added dropwise to the mixture within 10 minutes 21 ml of water and then 210 ml of 10% sulphuric acid. The aqueous phase was separated and extracted twice with diethyl ether. The combined organic phases were washed once with water and once with saturated sodium chloride solution, dried over sodium sulphate and evaporated. 39.2 g of 3-(trans-4-pentylcyclohexyl)-1-propanol were obtained as a colourless oil.

(d) 70.2 g of pyridinium chlorochromate were suspended in 506 ml of methylene chloride in a sulphonation flask under nitrogen gasification and then treated while stirring well within 5 minutes through a dropping funnel with a solution of 39.2 g of 3-(trans-4-pentylcyclohexyl)-1-propanol in 60 ml of methylene chloride. The dropping funnel was rinsed with 20 ml of methylene chloride and then the mixture was stirred at room temperature and under nitrogen gasification for 2.5 hours. Thereafter, 225 ml of absolute diethyl ether were added and the mixture was stirred at room temperature for a further 15 minutes. The supernatant solution was decanted off from the viscous black precipitate and the sulphonation flask was rinsed four times with 110 ml of absolute diethyl ether each time. The combined organic phases were chromatographed using diethyl ether as the eluent. The greenish oil (34.1 g) obtained after evaporation in vacuo was distilled in a high vacuum under nitrogen, there being obtained 28.1 g of 3-(trans-4-pentylcyclohexyl)propionaldehyde as a colourless crystallizing oil (b.p. 90°–99° C./0.08–0.1 mmHg).

(e) 58.2 g of trans-2-hexenyl-triphenylphosphonium bromide were suspended in 219 ml of absolute diethyl ether in a sulphonation flask under nitrogen gasification, cooled to 1° C. and treated dropwise within 25 minutes at 1°–4° C. through a dropping funnel with 89.4 ml of a 1.6M solution of butyl lithium in hexane and with 41 ml of absolute diethyl ether. The dropping funnel was rinsed with 17 ml of absolute diethyl ether and the mixture was stirred at 0° C. for 30 minutes. A solution of 28.1 g of 3-(trans-4-pentylcyclohexyl)propionaldehyde in 68.5 ml of absolute diethyl ether was subsequently added dropwise within 30 minutes at 3°–4° C. through the dropping funnel and the dropping funnel was then rinsed with 17 ml of absolute diethyl ether. The suspension obtained was stirred at 0° C. for a further 2 hours and at room temperature for 1 hour, then rinsed into a round flask with diethyl ether and concentrated in vacuo. The residue was rinsed with 410 ml of methanol/water (volume ratio 6:4) into a separating funnel and extracted three times with hexane. The hexane phases were washed once with 410 ml of methanol/water (volume ratio 6:4) and twice with 250 ml of water each time, dried over sodium sulphate and evaporated. Chromatography of the resulting brownish oil (38.5 g) on silica gel using hexane as the eluent finally gave 32.7 g of 1-(trans-4-pentylcyclohexyl)-3,5-trans-nonadiene (cis/trans ratio for the double bond in the 3,4-position 46:52.4) as a colourless oil.

(f) 9.5 g of 1-(trans-4-pentylcyclohexyl)-3,5-trans-nonadiene were dissolved in 62 ml of tetrahydrofuran in a round flask and treated with 14 mg of hydroquinone. A solution of 3.2 g of dicyanoacetylene in 18 ml of tetrahydrofuran was subsequently added by means of a pipette and the pipette was rinsed twice with 9 ml of tetrahydrofuran each time. The mixture was stirred at room temperature for 2.5 hours and then overnight at 40°–45° C. (bath temperature) under nitrogen. The dark brown solution was thereafter concentrated in vacuo. The resulting dark brown oil (10.9 g) was chromatographed on silica gel using hexane, hexane/toluene (volume ratio 1:1) and toluene, there being obtained 4.2 g of unreacted 3-cis, 5-trans-diene as a colourless oil and 7.4 g of 1,2-dicyano-3-[2-(trans-4-pentylcyclohexyl)ethyl]-6-propyl-1,4-cyclohexadiene as a slightly yellowish oil.

The trans-2-hexenyl-triphenylphosphonium bromide used above in paragraph (e) was prepared as follows:

(g) Dry carbon dioxide was introduced into a solution of 84.3 g of trans-2-hexen-1-ol in 253 ml of petroleum ether in a sulphonation flask, the solution was then cooled to −15° C. and treated dropwise at this temperature within 1 hour with a solution of 155.8 g of phosphorus tribromide in 253 ml of petroleum ether. The mixture was stirred, the temperature being held at −15° C. for a further 2 hours and then being allowed to rise to 0° C. within 5 hours and to room temperature overnight. The mixture was subsequently poured onto 1 l of ice/water. The aqueous phase was separated and extracted three times with 250 ml of petroleum ether each time. The combined organic phases were washed in sequence with 250 ml of saturated sodium chloride solution, 250 ml of saturated sodium hydrogen carbonate solution and 250 ml of saturated sodium chloride solution, dried over sodium sulphate, filtered and concentrated. A residue of 134.6 g of 1-bromo-2-hexene in the form of a yellowish oil were obtained.

(h) 200 g of triphenylphosphine were dissolved in 1 l of benzene in an Erlenmeyer flask and treated with 134.6 g of 1-bromo-2-hexene. The product began to crystallize after a few minutes. The mixture was left to stand at room temperature for a further 2 days. The precipitate was subsequently filtered off under suction, washed with benzene and petroleum ether and dried in vacuo over potassium hydroxide. The resulting crude product (292.6 g) was recrystallized from ethanol, boiled up with diethyl ether, filtered off under suction, dried in vacuo over potassium hydroxide, then pulverized and again dried in a high vacuum over phosphorus pentoxide. The product obtained was 209.9 g of trans-2-hexenyl-triphenylphosponium bromide as a colourless powder; m.p. 146° C. Working-up of the mother liquors gave a further 74.7 g of product.

The following compounds were manufactured in an analogous manner:

2,3-Dicyano-4-propyl-4'-pentylbiphenyl; m.p. 61.4° C.;
2',3'-dicyano-4-pentyl-4''-propyl-p-terphenyl; m.p. 134.9° C.;

The following compounds can be manufactured in an analogous manner:

2,3-Dicyano-1-[2-(trans-4-pentylcyclohexyl)ethyl]-4-butylbenzene; m.p. 71.8° C.;
2,3-dicyano-1-[2-(trans-4-propylcyclohexyl)ethyl]-4-hexylbenzene; m.p. 67.6° C.;
2,3-dicyano-1-[2-(p-pentylphenyl)ethyl]-4-propylbenzene; m.p. 75.7° C.

We claim:

1. A compound of the formula:

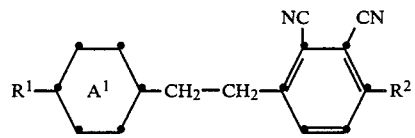

wherein $R^1$ and $R^2$ are independently straight-chain $C_1$–$C_{12}$-alkyl or $R^2$ may also independently be straight-chain $C_1$–$C_{12}$-alkoxy, and ring $A^1$ is trans-1,4-cyclohexylene.

2. The compound of claim 1, wherein $R^1$ is straight-chain $C_1$–$C_{12}$-alkyl and $R^2$ is straight-chain $C_1$–$C_{12}$-alkoxy.

3. The compound of claim 1, wherein $R^1$ and $R^2$ are straight-chain $C_1$–$C_{12}$-alkyl.

4. The compound of claim 1, wherein the compound is 2,3-dicyano-1-[2-(trans-4-pentylcyclohexyl)ethyl]-4-propyl-benzene.

5. The compound of claim 1, wherein the compound is 2,3-dicyano-1-[2-(trans-4-pentylcyclohexyl)ethyl]-4-butylbenzene.

6. A liquid crystalline mixture comprising
(a) at least one compound of the formula:

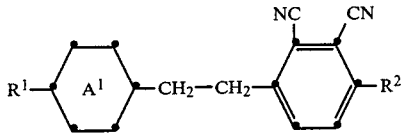

wherein $R^1$ and $R^2$ are independently straight-chain $C_1$–$C_{12}$-alkyl; or $R^2$ may also independently be straight-chain $C_1$–$C_{12}$-alkoxy; and ring $A^1$ is trans-1,4-cyclohexylene; and (b) at least one additional liquid crystalline substance.

7. The liquid crystalline mixture of claim 6 wherein the additional liquid crystalline substance is a liquid crystalline carrier material having a dielectric anisotropy of at most about +1.

8. The liquid crystalline mixture of claim 6 comprising three components A, B and C, each of which comprises at least one compound, wherein component A has a viscosity of at most about 40 cp, a clearing point of at least about 40° C. and a dielectric anisotropy between about −2 and about +1, component B has a dielectric anisotropy below about −2 and comprises at least one compound of formula I, and component C has a dielectric anisotropy above about +10, a clearing point of at least about 100° C. and a cross-over frequency in the total mixture of at most about 15 kHz at about 20° C.

9. An electro-optical cell comprising:
(a) two plate means;
(b) a liquid crystal means disposed between the two plate means and including a compound of the formula:

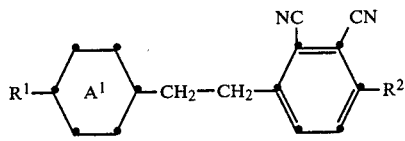

wherein $R^1$ and $R^2$ are independently straight-chain $C_1$–$C_{12}$-alkyl or $R^2$ may also independently be straight-chain $C_1$–$C_{12}$-alkoxy, and ring $A^1$ is trans-1,4-cyclohexylene; and
(c) means for applying an electrical potential to said plate means.

* * * * *